(12) United States Patent
Bassan et al.

(10) Patent No.: US 8,911,458 B2
(45) Date of Patent: Dec. 16, 2014

(54) DEVICE FOR PERFORMING END-TO-END ANASTOMOSIS

(75) Inventors: Harmanpreet Bassan, Toronto (CA); Peter Kim, Totonto (CA); Thomas Looi, Markham (CA)

(73) Assignee: The Hospital for Sick Children, Toronto (CA)

( * ) Notice: Subject to any disclaimer, the term of this patent is extended or adjusted under 35 U.S.C. 154(b) by 851 days.

(21) Appl. No.: 13/158,020

(22) Filed: Jun. 10, 2011

(65) Prior Publication Data

US 2011/0306994 A1 Dec. 15, 2011

Related U.S. Application Data

(60) Provisional application No. 61/353,974, filed on Jun. 11, 2010.

(51) Int. Cl.
*A61B 17/11* (2006.01)

(52) U.S. Cl.
USPC ........... 606/153; 606/138; 606/144; 606/149; 606/219; 227/175.1; 227/176.1; 227/179.1

(58) Field of Classification Search
USPC ............. 606/144, 184, 151, 153, 219, 1, 139; 227/176.1, 175.1, 179.1
See application file for complete search history.

(56) References Cited

U.S. PATENT DOCUMENTS

| | | | |
|---|---|---|---|
| 6,358,258 B1 | 3/2002 | Arcia et al. | |
| 7,029,481 B1 | 4/2006 | Burdulis, Jr. et al. | |
| 7,585,307 B2 * | 9/2009 | Fontayne et al. | 606/153 |
| 8,002,780 B2 * | 8/2011 | Yossepowitch et al. | 606/144 |
| 2008/0275472 A1 | 11/2008 | Yossepowitch et al. | |

* cited by examiner

*Primary Examiner* — Vy Q Bui
(74) *Attorney, Agent, or Firm* — Lynn C. Schumacher; Hill & Schumacher

(57) ABSTRACT

Herein is provided an anastomosis device which includes a cylindrical support housing having a tapered section being formed of a plurality of compliant fingers integrally formed around the circumference of an end of the cylindrical section which can flex at their connection point to the cylindrical section. Each compliant finger holds a suture needle. The device includes a push rod having a cam head at one end of the rod section. The cam head is located adjacent to the tapered portion. In operation the anastomosis device is aligned with the anatomical tubular structure undergoing an anastomosis process. When a back end of the push rod is pushed towards the tapered section of the support housing, the cam head section bears against an inner surface causing each compliant finger to flex radially outwards forcing the suture needles to simultaneously pierce the wall of the anatomical tubular structure.

16 Claims, 6 Drawing Sheets

DEVICE FOR PERFORMING END-TO-END ANASTOMOSIS

CROSS REFERENCE TO RELATED U.S. PATENT APPLICATION

This patent application relates to U.S. provisional patent application Ser. No. 61/353,974 filed on Jun. 11, 2010, entitled DEVICE FOR PERFORMING END-TO-END ANASTOMOSIS, filed in English, which is incorporated herein in its entirety by reference.

FIELD OF THE INVENTION

The present disclosure relates to a device for accomplishing the surgical process of anastomosis i.e. connecting two structures (commonly tubular structures) to restore continuity after resection or to bypass an unresectable disease process. More particularly the present disclosure relates to a device and process for connecting the structures in an end-to-end fashion.

BACKGROUND OF THE INVENTION

A common requirement in many surgical procedures is the resection or bypass of a diseased organ. Often the diseased section is a part of a tubular structure (e.g. artery, bowel, esophagus) and after the resection it is required to reattach the resulting two healthy ends. This procedure is termed as anastomosis and is a fairly easy task to perform in the setting of an open surgery. However, in minimally invasive surgery (MIS) where the procedure is performed through small incisions in the patient's skin, anastomosis is an extremely difficult skill to learn and execute. Typical anastomosis time in a MIS procedure ranges anywhere from half an hour up to two hours. Needless to say, the long anastomosis time has a negative impact on the patient due to increased anesthesia requirement. For the surgeon, laparoscopic anastomosis is extremely difficult to learn and perform, and is very fatiguing in nature. Increased anastomosis time is also a burden on the healthcare provider as it takes up valuable operating room time and adds to the personnel cost.

U.S. Pat. No. 6,358,258 issued to Arcia et al. discloses an anastomosis device that utilizes multiple flexible needles (designed of Nitinol material) that are deployed through multiple curved guide channels. The design utilizes multiple push rods for actuation and is suitable for end-side type anastomosis.

U.S. Pat. No. 7,029,481 issued to Burdulis et al. discloses an anastomosis device that utilizes multiple needles that are simultaneously pierced through the tissue using a pneumatic cylinder. The needles latch onto small crimps on the opposite end and pull the sutures through the tissue upon retraction. The other end of the device utilizes multiple flexible needles deployed using curved channels and multiple push rods. The design needs custom needles as the sutures are attached to the distal tip of the needle as opposed to the proximal end found in conventional sutures.

U.S. Patent Application US2008/0275472, to Yossepowitch et al. discloses an anastomosis device that utilizes multiple needle deployment through the use of flexible needle and curved guide channels. The design utilizes multiple push rods and requires custom needles to function. Even though the two ends of the design are attached through a flexible coupler, the design lacks a good suture management scheme and will suffer from suture tangling. Similar to U.S. Pat. No. 7,029,481, the design needs custom needles as the sutures are attached to the distal tip of the needle as opposed to the proximal end found in conventional sutures.

Thus, there is a need for an automated/assisted laparoscopic anastomosis device that can reduce procedure time and operating costs. The device will also be of interest to the surgeons as it would minimize the dependence on a surgeon's dexterity and experience and will reduce the learning curve of this complex task.

SUMMARY OF THE INVENTION

The present disclosure provides an anastomosis device, comprising:

a) a support housing having an interior chamber and having a longitudinal axis, said support housing having a compliant flexible section, and a plurality of suture needles mounted on an outer surface of said compliant flexible section, said suture needles being aligned with, and around, said longitudinal axis;

b) an introducer including a circular disc section rigidly affixed to said support housing adjacent to an end of the compliant flexible section, the circular disc section having a diameter selected to match an interior diameter of an anatomical tubular structure undergoing an anastomosis process; and c) a deformation mechanism mounted in said interior chamber and configured such that when said introducer is seated in said anatomical tubular structure and the deformation mechanism is activated the deformation mechanism bears outwardly against an interior surface of said compliant flexible section to drive said plurality of suture needles radially outwards away from the longitudinal axis forcing said plurality of suture needles to pierce through a wall of the anatomical tubular structure simultaneously around a circumference of said anatomical tubular structure.

In a further embodiment of the present invention, there is provided an anastomosis device, comprising:

a) a support housing having an interior chamber and having a cylindrical section having a longitudinal axis and a tapered section, the tapered section being formed of a plurality of compliant fingers integrally formed around a circumference of an end of the cylindrical section and tapering down from a diameter of said cylindrical section toward said longitudinal axis, a connection of each compliant finger to said cylindrical section being designed to flex, each of said compliant fingers having a lengthwise groove to receive therein a longitudinal section of a suture needle with a curved end portion of each suture needle located at a distal end of said compliant finger and sutures being attached to the longitudinal section of each suture needle;

b) an introducer including a disc section rigidly affixed to said support housing adjacent an end of the tapered section, the disc section having a diameter selected to match an interior diameter of an anatomical tubular structure undergoing an anastomosis process; and c) a push rod including a rod section and a cam head section at one end of the rod section and the push rod having a passageway extending therethrough, the push rod being seated in said interior chamber with the cam head section located adjacent to said tapered portion, wherein in operation the anastomosis device is aligned with the anatomical tubular structure undergoing an anastomosis process with the disc section of the introducer being inserted into an end of the anatomical tubular structure and the anastomosis device is inserted far enough to ensure the curved ends of the plurality of suture needles are at least a pre-selected distance from the end of the anatomical tubular structure, and when so located, when a back end of the push rod section is pushed towards the tapered section of the support housing the cam head section bears against an inner surface each of the plurality of compliant fingers causing each compliant finger flex radially outwards forcing the plurality of suture needles to simultaneously pierce circumferentially through a wall of the anatomical tubular structure.

In a further embodiment of the present invention, there is provided an anastomosis device, comprising:

a) a support housing having an interior chamber and having a longitudinal axis, said support housing having a compliant flexible section, and a plurality of suture needles mounted on an outer surface of said compliant flexible section, said suture needles being aligned with, and around, said longitudinal axis, said support housing including a cylindrical section having first and second opposed ends, wherein said compliant flexible section is a tapered section attached at said first opposed end, the tapered section being formed of a plurality of compliant fingers integrally formed around a circumference of said first end of the cylindrical section and tapering down from a diameter of said cylindrical section toward said longitudinal axis, a connection of each compliant finger to said first section being designed to flex radially outwardly when the deformation mechanism bears against the inner surface of said plurality of compliant fingers, b) an introducer including a circular disc section rigidly affixed to said support housing adjacent to an end of the compliant flexible section, the circular disc section having a diameter selected to match an interior diameter of an anatomical tubular structure undergoing an anastomosis process; and c) a deformation mechanism in said interior chamber, said deformation mechanism comprising a push rod integrally formed with said plurality of compliant fingers, said push rod aligned with said longitudinal axis, said compliant fingers tapering down from said diameter of said cylindrical section towards a front end of said push rod to join with said front end of said push rod, said deformation mechanism configured such that when said introducer is seated in said anatomical tubular structure and a back end of said push rod is pushed towards said tapered section of said support housing said plurality of compliant fingers flex outwards forcing the plurality of suture needles to simultaneously pierce said anatomical tubular structure.

In a further embodiment of the present invention, there is provided an anastomosis surgical kit, comprising an anastomosis device and a laparoscopic deployment tool.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Without limitation, the majority of the systems described herein are directed to an anastomosis device and method of using the same. As required, embodiments of the present invention are disclosed herein. However, the disclosed embodiments are merely exemplary, and it should be understood that the invention may be embodied in many various and alternative forms.

The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an anastomosis device and method of using the same.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region. For example, in embodiments of the present invention dimensions of components of an anastomosis device are given but it will be understood that these are not meant to be limiting.

Figure 1:
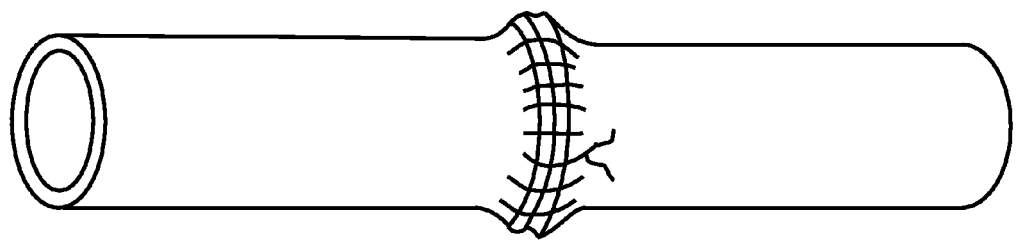
FIG. 1 shows an exemplary embodiment of two tubular structures after the anastomosis has been performed.

As used herein, the process of "anastomosis" refers to the process of reattaching two healthy ends of an anatomical tubular structure (such as blood veins, arteries, intestines etc.) after a resection has been carried out to remove a diseased or injured section. FIG. 1 shows an exemplary embodiment of two tubular structures after the anastomosis has been performed.

As used herein, the phrase "anastomosis device" refers to a device for performing the process of anastomosis which forms the subject matter of the present invention.

Figure 2:
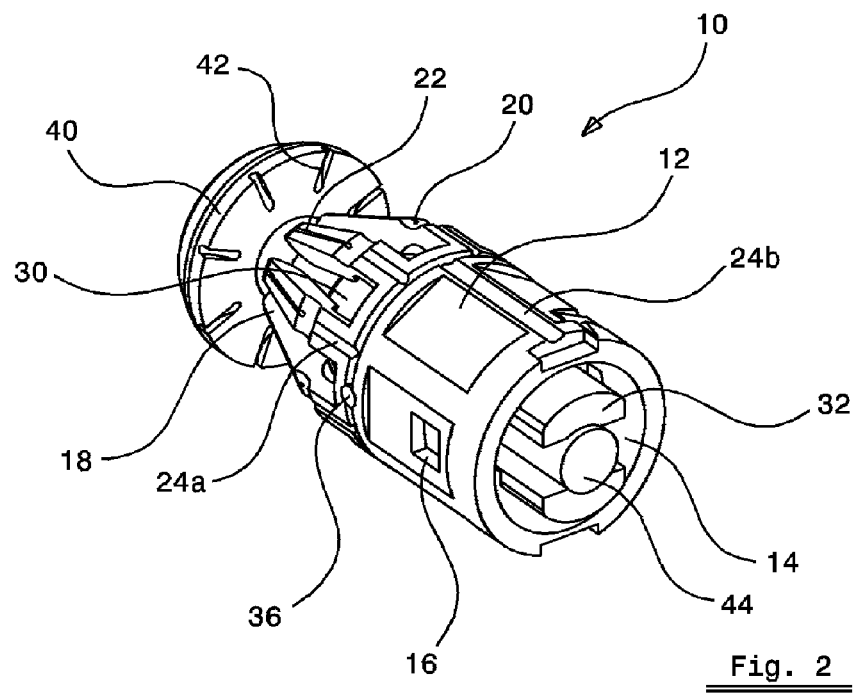
FIG. 2 is a perspective view of an embodiment of an anastomosis device constructed in accordance with the present invention.

Herein is disclosed an anastomosis device that facilitates the task of tissue approximation through simultaneous deployment of multiple sutures in a circumferential fashion. FIG. 2 shows the preferred embodiment of the anastomosis device 10. The disclosed anastomosis device 10 uses conventional sutures with a flexible center support 12. The center support 12 is designed of compliant material (preferably plastics) and performs two functions in the system: it holds the needles in place (in its collapsed form) and it bends outward to allow the needles to pierce the tissue (when deployed). FIG. 2 shows the disclosed anastomosis device 10 with the center support 12 in its collapsed form. The center support 12 includes an opening 14 and two latches 16 on the proximal end. The opening 14 and latches 16 are utilized to attach the anastomosis device 10 to a laparoscopic deployment tool 80 shown in FIG. 6 (explained later).

The center support 12 includes a plurality of compliant fingers 18 that are designed to flex at one section (preferably 20) along its length. Each finger 18 is capable of holding a needle in groove 22. The introducer 40 allows easy insertion of the anastomosis device 10 into the target anatomy and throughout the deployment process keeps the needles properly aligned using grooves 42. Introducer 40 and center support 12 are rigidly attached to each other through the use of a pin 36 and a hole 46 (FIG. 4) and therefore act as a single entity in the mechanism. The center support 12 can also include suture management channels 24a and 24b (in the form of grooves) that minimize problems such as suture tangling. The push rod 32 includes a cam head 30 and is designed such that it can easily translate into and out of the center support 12 through the use of a laparoscopic deployment tool. The proximal shaft 44 of the introducer 40 acts as a guiding means for push rod 32.

Figure 3:
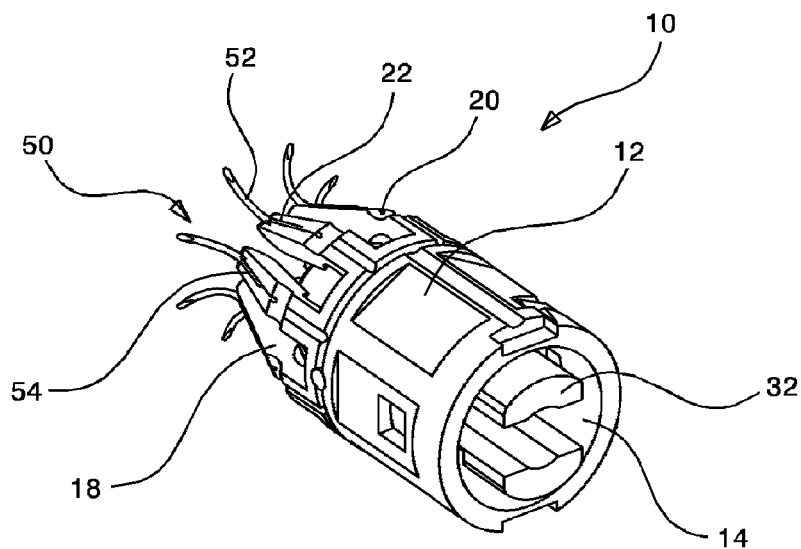
FIG. 3 is a perspective view of the device of FIG. 2 but absent a component to show a plurality of suture needles which form part of the device.
Figure 4:
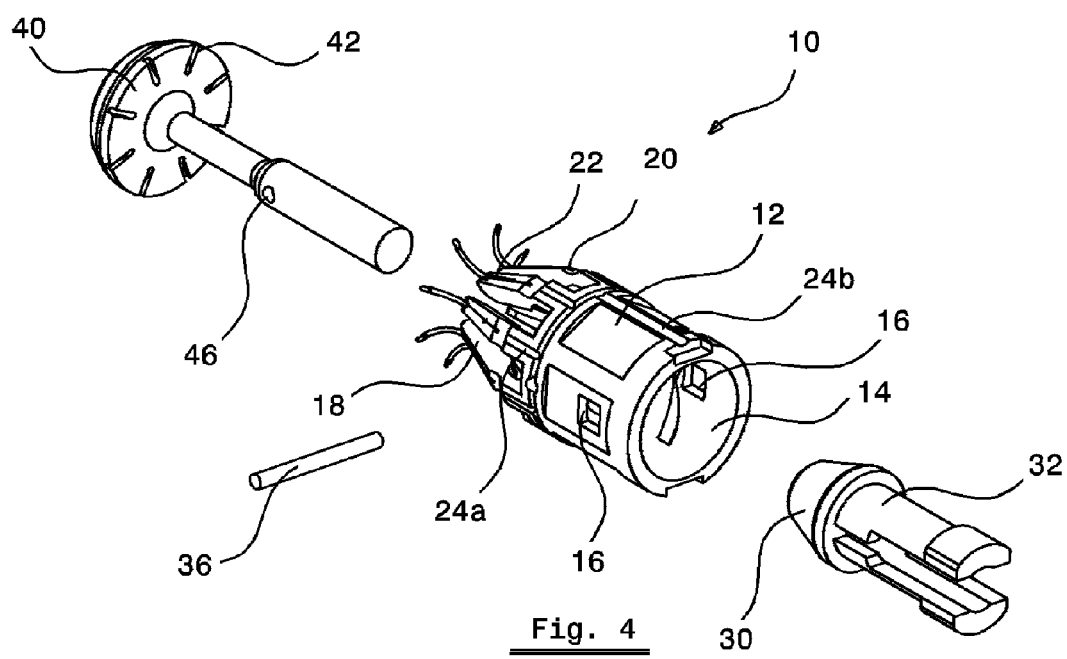
FIG. 4 shows an exploded perspective view of the device of FIG. 2.

FIG. 3 shows the preferred embodiment of the anastomosis device showing the needles 50 (introducer 40 hidden for brevity) mounted on the housing support 12. One preferred embodiment of needle 50 will include a ¾ circular section 52 and a straight profile 54 that would snug fit into groove 22. FIG. 4 shows a view of the anastomosis device disassembled showing more details of the introducer 40 and the push rod 32.

Figure 5:
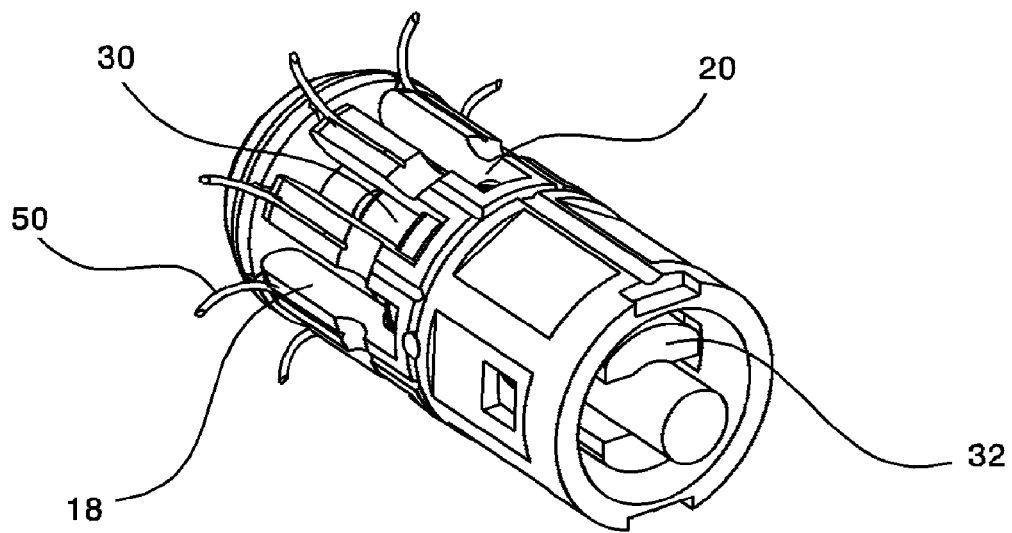
FIG. 5 shows a perspective view of the anastomosis device in its deployed configuration.

FIG. 5 shows the anastomosis device 10 in its deployed form. It can be noticed that in order to deploy the sutures, the push rod 32 linearly translates towards the distal end of the center support 12 along its longitudinal axis. As the push rod 32 translates, cam surface 30 applies an outward acting force on flexible fingers 18 of the center support 12. Flexible fingers 18 are designed so as to bend at a certain section 20 along their length (defined by a slightly narrow profile) and as a result that area acts as a hinge joint for the fingers. The resulting effect is the simultaneous outward motion of needles 50 and piercing of the target vessel. Optionally, push rod 32 can be designed with a built in locking mechanism so that it stays in its distal position after the deployment and the laparoscopic deployment tool can be released from center support 12.

Figure 6:
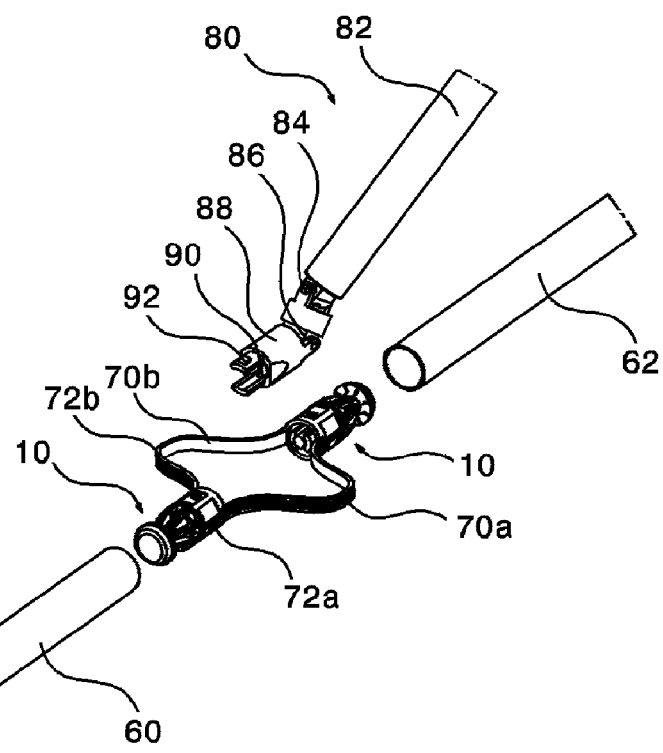
FIG. 6 shows a perspective view of the anastomosis device configured to be deployed to perform an end-end anastomosis using a laparoscopic deployment tool.

FIG. 6 shows a scenario where the anastomosis device is deployed to perform an end-end anastomosis. It can be seen that in the preferred embodiment two center supports 10 are attached to each other through two flexible couplings 70a and 70b. The flexible couplings 70a and 70b are made of compliant material, preferably plastic. The flexible couplings 70a and 70b have two functions: to retain the center supports 10 and to provide a path for suture routing and management. In the preferred embodiment, half of the sutures 72a from center support 10 can be routed on coupling 70a and other half 72b on coupling 70b to the second center support 10. It is noted that 72a and 72b are multiple sutures. Each of 72a and 72b may contain three (3) or more sutures; as such, the anastomosis device 10 may have a total of six (6) or more sets of needles and sutures.

Note that a suture from a needle 50 on the first support 10 is terminated at the respective needle 50 on the second support system 10. The flexible couplings 70a and 70b therefore allows these sutures to be routed from first center support 10 to the second center support 10 while minimizing problems such as suture tangling etc. At the same time, flexible couplings 70a and 70b allow needle deployment in cases where the two healthy ends of vessels 60 and 62 are not in a perfect alignment.

FIG. 6 also shows a laparoscopic deployment tool 80 that is designed with a dexterous end-effector 88. The dexterous end-effector 88 allows the center support 12 to be oriented in multi degrees-of-freedom utilizing two joints 84 and 86 for easy introduction into the target vessel. Once inserted, the laparoscopic deployment tool 80 gets latched to the center support 10 through the use of keys 92 and latches 16 to maintain a firm contact. The surgeon then uses the laparoscopic deployment tool 80 to introduce the center support 10 into the target vessel (60 or 62). The dexterous end-effector 88 is preferably cylindrical shaped and includes a push rod 90. In one embodiment, push rod 90 can be an integrated unit with a small actuator built into it. In another embodiment, push rod 90 can be actuated using a cable based mechanism that routes through the two joints 84 and 86 with the actuator located on the proximal end of the tool 80. The laparoscopic deployment tool 80 can also include another cable that is routed through joints 84 and 86 and once actuated causes a radial motion of keys 92 towards the longitudinal axis of the dexterous end-effector 88. Once anastomosis tool 10 and laparoscopic tool 80 are latched, the actuator translates the push rod 90 such that it comes in contact with push rod 32 (inside tool 10) and causes a linear motion of cam surface 30 in the direction of distal end. As a result, compliant fingers 18 deform and needles 50 pierce through the vessel (60 or 62). The laparoscopic tool 80 can then be de-latched from anastomosis tool 10 using the cable actuation for keys 92, retracted from the vessel (60 or 62) and inserted into the other vessel to deploy the second set of needles.

Figure 7:
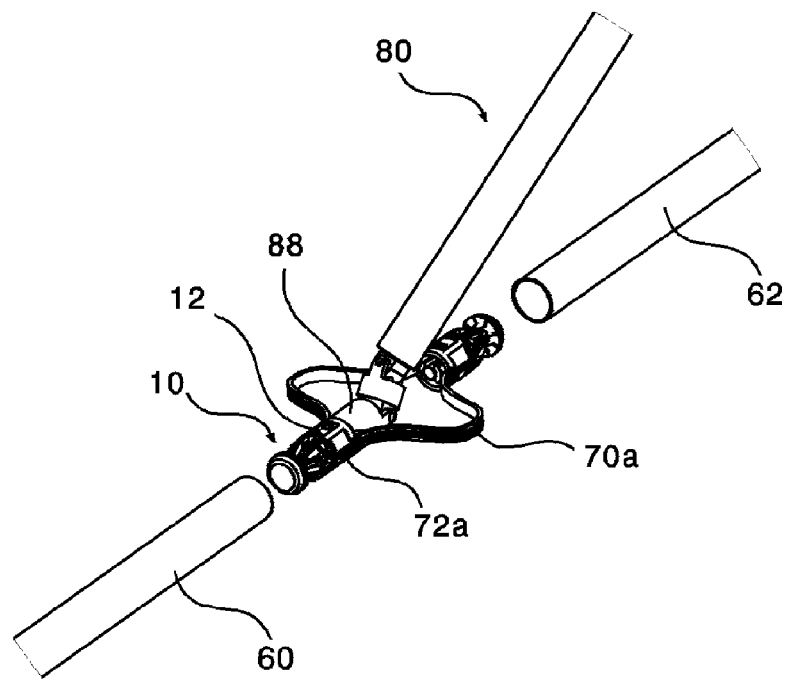
FIG. 7 shows the laparoscopic deployment tool of FIG. 6 latched to the anastomosis device and ready to be inserted into the first healthy end of a vessel.

FIG. 7 shows the laparoscopic deployment tool 80 latched to the anastomosis device 10 and ready to be inserted into the first healthy end 60 of the vessel. The size of introducer 40 is such that it facilitates easy insertion into the first healthy end 60 of the tubular anatomical structure.

Figure 8:
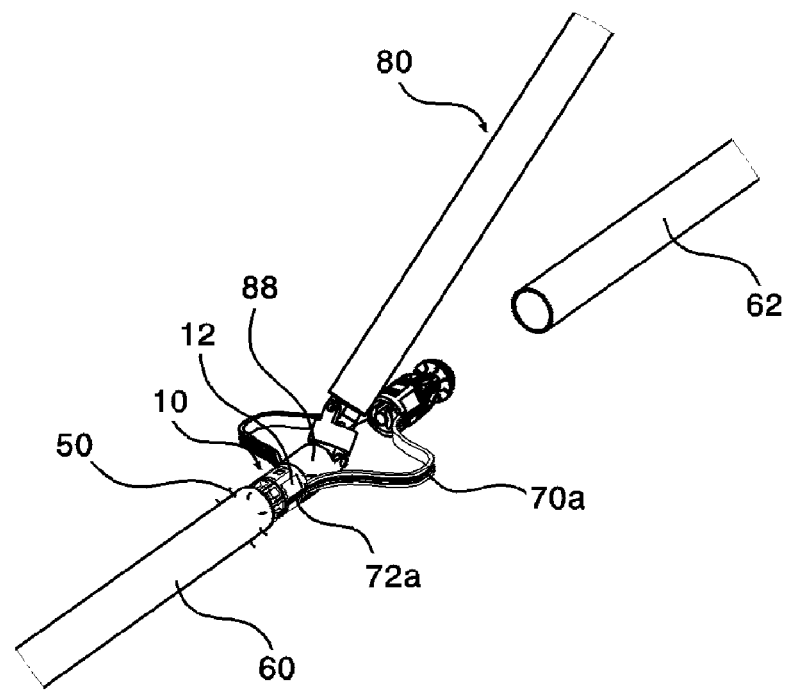
FIG. 8 shows the anastomosis device after it has been inserted into the first healthy end of a vessel and has been deployed through the use of the laparoscopic deployment tool.

FIG. 8 shows the anastomosis device 10 after it has been inserted into the first healthy end 60 and needles 50 have been deployed through the use of the laparoscopic deployment tool 80 using push rod 90. As can be seen from the figure, actuation of the laparoscopic deployment tool 80 causes the push rod 90 to linearly translate and in effect cause the linear translation of the push rod 32 inside the anastomosis device 10. The translation of push rod 32 causes the cam surface 30 to apply a simultaneous outward acting force on flexible fingers 18 which in turn cause needles 50 to puncture the first healthy end 60. The surgeon then disengages the laparoscopic deployment tool 80 from 12 and inserts it into the other unit 10 (towards end 62).

Figure 9:
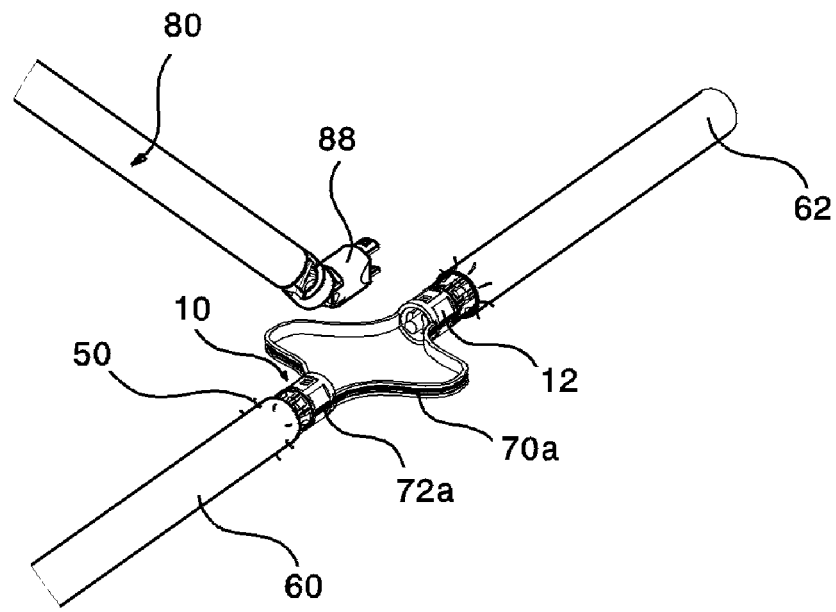
FIG. 9 shows a perspective view of the anastomosis device where the suture needles have been deployed on each of vessels being sutured together with the laparoscopic deployment tool being retracted.

FIG. 9 shows the case where needles 50 have been deployed on each end and the laparoscopic deployment tool 80 has been retracted from anastomosis device 10. The surgeon can then use standard laparoscopic graspers to pull needles 50 and sutures 72a and 72b through the tissues 60 and 62. Once this step is complete, the center support 10 from each end of the vessel is extracted and the surgeon performs the knot tying on the sutures using standard methods. In another embodiment, a secondary automated tool can be used to assist in knot-tying task to make the procedure easier and expedite the anastomosis process.

Figure 10:
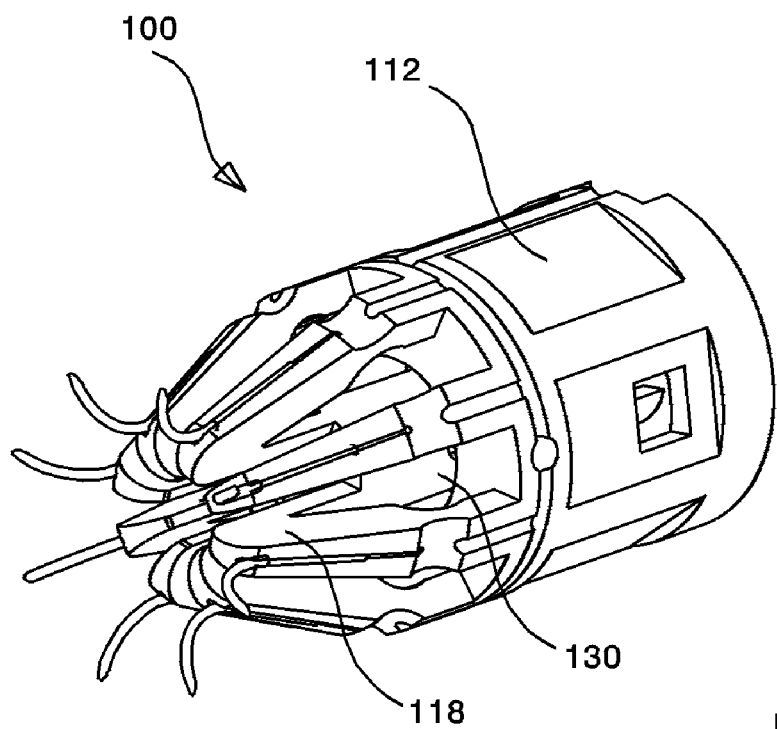
FIG. 10 is a perspective view of a second embodiment of an anastomosis device constructed in accordance with the present invention.
Figure 11:
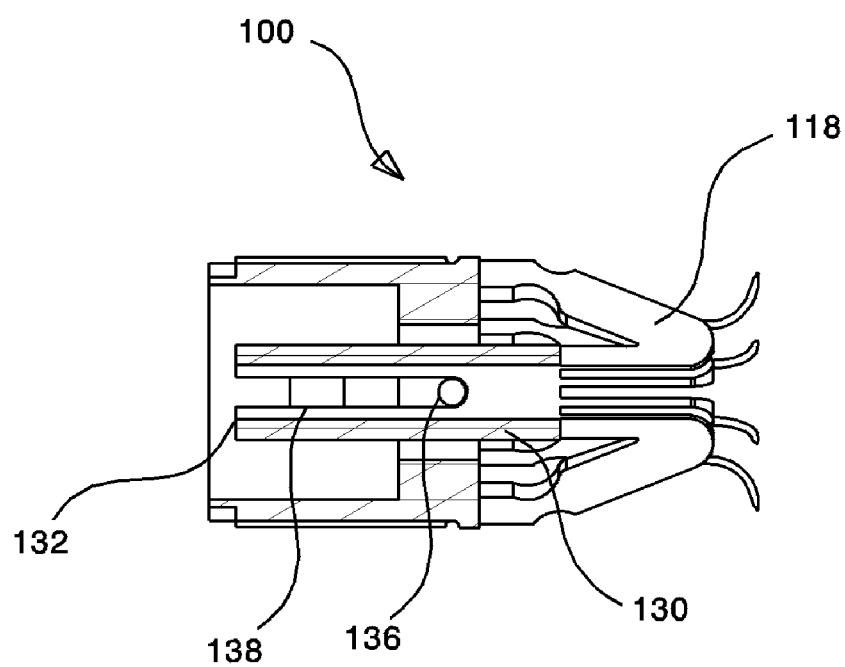
FIG. 11 shows a section view of the device of FIG. 10.

FIG. 10 is a perspective view of a second embodiment of an anastomosis device 100 constructed in accordance with the present disclosure. In this embodiment, the separate push rod 32 (including cam surface 30) of FIG. 2 has been eliminated from the device. Instead, the functionality of push rod 32 has been achieved through the redesign of compliant fingers 118 on the device to include integrated push rod 130. In this embodiment, compliant fingers 118 are designed such that they all merge and join at a single push rod 130. Push rod 130 is preferably designed as a hollow cylindrical shaft with a cut out section 138 (FIG. 11). Push rod 130 acts as an integral component with compliant fingers 118 while translating freely over pin 136 (that joins flexible support 112 and introducer 40 (FIG. 2)). Once device 100 is latched to laparoscopic tool 80, push rod 90 applies an axial force at surface 132 of push rod 130 which causes the compliant fingers 118 to flex radially outwards and causes needles 50 to puncture the tissue. This design results in a device that is substantially cheaper to produce while achieving a similar functionality.

FIG. 11 shows a section view of the device of FIG. 10 showing the cut out section 138, pin 136 and surface 132.

The anastomosis device 10 uses a flexible center support system that can be easily manufactured using low cost materials such as plastics. The system design is simple and therefore can be mass produced at low cost using standard fabrication techniques such as injection molding. The design utilizes conventional needles and sutures and does not require custom materials as needed in some other designs. The center support system is the low cost component and is therefore designed as a one-time use disposable device. The laparoscopic deployment tool 80 can be designed such that it can be re-sterilized and reused. Thus the anastomosis device 10 and laparoscopic deployment tool 80 may be sold separately or together as a kit.

Manual suturing is still considered a gold standard for anastomosis and the anastomosis device disclosed herein and its method of use will have a good acceptance amongst surgeons.

The anastomosis device 10 and the laparoscopic deployment tool 80 have a good market potential that is evident from the fact that even after centuries of technological development, only a handful of automated/assisted anastomosis devices exist in the market. Most of these devices are designed for open surgery and find little or no use in an MIS approach. MIS has already become a preferred surgical approach due to its benefits to the patient. It is evident that the number of procedures performed through this approach will increase in the coming years. At the same time, without any improvement to the laparoscopic anastomosis technique, present anastomosis time of the order of hours will have a huge social and financial burden. Thus an anastomosis device that can potentially reduce anastomosis time from hours to minutes will have a good market potential and financial value.

The anastomosis device 10 disclosed herein has advantages over existing devices and technologies in terms of its simplicity and low cost. The anastomosis device 10 is also suitable for varying diameter arteries/vessels and can be scaled up or down to account for those differences.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An anastomosis device, comprising:
   a) a support housing having an interior chamber and having a longitudinal axis, said support housing having a compliant flexible section, and a plurality of suture needles mounted on an outer surface of said compliant flexible section, said plurality of suture needles being aligned with, and around, said longitudinal axis;
   b) an introducer including a circular disc section rigidly affixed to said support housing adjacent to an end of said compliant flexible section, said circular disc section having a diameter selected to match an interior diameter of an anatomical tubular structure undergoing an anastomosis process; and
   c) a deformation mechanism mounted in said interior chamber and configured such that when said introducer is seated in said anatomical tubular structure and said deformation mechanism is activated said deformation mechanism including a cam head section bears outwardly away from said longitudinal axis against an interior surface of said compliant flexible section to drive said plurality of suture needles radially outwards away from said longitudinal axis forcing said plurality of suture needles to pierce through a wall of said anatomical tubular structure simultaneously around a circumference of said anatomical tubular structure.

2. The anastomosis device according to claim 1 wherein said support housing includes a cylindrical section having a first opposed end and a second opposed end, and wherein said compliant flexible section is a tapered section attached at said first opposed end, said tapered section being formed of a plurality of compliant fingers integrally formed around a circumference of said first opposed end of said cylindrical section and tapering down from a diameter of said cylindrical section toward said longitudinal axis, a connection of each compliant finger to said first opposed end said cylindrical section being designed to flex radially outwardly when said deformation mechanism bears against an inner surface of said plurality of compliant fingers.

3. The anastomosis device according to claim 2 wherein each of said plurality of compliant fingers has a lengthwise groove on said outer surface to receive therein a longitudinal section of one of said plurality of suture needles with a curved end portion of said one of said plurality of suture needles being located at a distal end of said compliant finger and sutures being attached to said longitudinal section of said one of said plurality of suture needles.

4. The anastomosis device according to claim 3 wherein said deformation mechanism comprises a push rod having a rod section and said cam head section at one end of said rod section and said push rod having a passageway extending therethrough, said push rod being seated in said interior chamber with said cam head section located adjacent to said tapered section, and wherein when a back end of said push rod section is pushed towards said tapered section of said support housing said cam head section bears against said inner surface each of said plurality of compliant fingers causing each compliant finger to flex radially outwards forcing said plurality of suture needles to simultaneously pierce through said wall of said anatomical tubular structure.

5. The anastomosis device according to claim 4 wherein said introducer includes a shaft section connected to said disc section, said shaft section being located in said interior chamber aligned along said longitudinal axis, and wherein said shaft section is located in said passageway of said push rod, and wherein when said push rod is driven forwards to outwardly flex said plurality of compliant fingers, said push rod slides along over said shaft section which is fixed.

6. The anastomosis device according to claim 5 wherein an inner surface of said disc section includes a plurality of slots equal to a number of suture needles mounted on said tapered section of said support housing, said slots being configured to receive said curved end portion of each suture needle.

7. The anastomosis device according to claim 3, wherein said deformation mechanism comprises a push rod integrally formed with said plurality of compliant fingers, said compliant fingers tapering down from said diameter of said cylindrical section towards a front end of said push rod to join with said front end of said push rod, wherein when a back end of said push rod is pushed towards said tapered section of said support housing said plurality of compliant fingers flex outwards forcing said plurality of suture needles to simultaneously pierce through said wall of said anatomical tubular structure.

8. An anastomosis device, comprising:
   a) a support housing having an interior chamber and having a cylindrical section having a longitudinal axis and a tapered section, said tapered section being formed of a plurality of compliant fingers integrally formed around a circumference of an end of said cylindrical section and tapering down from a diameter of said cylindrical section toward said longitudinal axis, a connection of each compliant finger to said cylindrical section being designed to flex, each of said compliant fingers having a lengthwise groove to receive therein a longitudinal section of a suture needle with a curved end portion of each suture needle located at a distal end of said compliant finger and sutures being attached to said longitudinal section of each suture needle;
   b) an introducer including a disc section rigidly affixed to said support housing adjacent to an end of said tapered section, said disc section having a diameter selected to match an interior diameter of an anatomical tubular structure undergoing an anastomosis process; and
   c) a push rod including a rod section and a cam head section at one end of said rod section and said push rod having a passageway extending therethrough, said push rod being seated in said interior chamber with said cam head section located adjacent to said tapered section, wherein in operation said anastomosis device is aligned with said anatomical tubular structure with said disc section of said introducer being inserted into an end of said anatomical tubular structure and said anastomosis device is inserted far enough to ensure said curved ends of said plurality of suture needles are at least a pre-selected distance from said end of said anatomical tubular structure, and when so located, when a back end of said push rod section is pushed towards said tapered section of said support housing and said cam head section bears against an inner surface each of said plurality of compliant fingers causing each compliant finger to flex radially outwards forcing said plurality of suture needles to simultaneously pierce circumferentially through a wall of said anatomical tubular structure.

9. The anastomosis device according to claim 8 wherein said introducer includes a shaft section connected to said disc section, said shaft section being located in said interior chamber and said shaft section being located in said passageway of said push rod.

10. The anastomosis device according to claim 9 wherein said introducer is held fixed within said support housing by a pin inserted through a first hole in said housing which is aligned with a second hole in said shaft section of said introducer.

11. The anastomosis device according to claim 10 wherein an inner surface of said disc section includes a plurality of slots equal to a number of suture needles mounted on said tapered section of said support housing, said slots being configured to receive said curved end portion of each suture needle.

12. The anastomosis device according to claim 11 wherein said support housing is made of a plastic material, said cylindrical section and said plurality of compliant fingers being made of said plastic material.

13. The anastomosis device according to claim 12 wherein said connection of each compliant finger to said cylindrical section being designed to flex is shaped to allow flexing of said compliant finger radially outward and inward with respect to said longitudinal axis at said connection of each compliant finger to said cylindrical section.

14. The anastomosis device according to claim 8 wherein said support housing includes suture management channels in which sutures are maintained until said suture needles are deployed.

15. The anastomosis device according to claim 14 configured to perform an end-end anastomosis, wherein said anastomosis device is a first anastomosis device, and including a second anastomosis device tethered to said first anastomosis device by at least one flexible coupling which is configured for releasably holding sutures for suture routing and management.

16. The anastomosis device according to claim 15 wherein said at least one flexible coupling is two flexible couplings, and wherein a suture terminated at one end thereof on a suture needle mounted on said first anastomosis device is terminated at its other end on a respective suture needle mounted on said second anastomosis device.

* * * * *